United States Patent
Sakamoto

(10) Patent No.: US 10,002,423 B2
(45) Date of Patent: Jun. 19, 2018

(54) MEDICAL IMAGE PROCESSING APPARATUS, MEDICAL IMAGE PROCESSING METHOD, AND MEDICAL IMAGE PROCESSING SYSTEM

(71) Applicant: CANON KABUSHIKI KAISHA, Tokyo (JP)

(72) Inventor: Tsuyoshi Sakamoto, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days. days.

(21) Appl. No.: 15/252,891

(22) Filed: Aug. 31, 2016

(65) Prior Publication Data

US 2017/0069085 A1 Mar. 9, 2017

(30) Foreign Application Priority Data

Sep. 4, 2015 (JP) .................. 2015-174592
Sep. 4, 2015 (JP) .................. 2015-175036

(51) Int. Cl.
*G06K 9/00* (2006.01)
*G06T 7/00* (2017.01)
(Continued)

(52) U.S. Cl.
CPC .......... *G06T 7/0012* (2013.01); *A61B 6/5294* (2013.01); *G06T 5/007* (2013.01);
(Continued)

(58) Field of Classification Search
CPC ..... G06T 7/0012; G06T 5/007; G06T 11/003; G06T 11/008; G06T 2207/10081;
(Continued)

(56) References Cited

U.S. PATENT DOCUMENTS 4,709,212 A 11/1987 MacFall
5,655,532 A 8/1997 Yasugi et al.
(Continued)

FOREIGN PATENT DOCUMENTS

JP 59-228152 A 12/1984
JP 61-249457 A 11/1986
(Continued)

OTHER PUBLICATIONS

Johnson, Thorsten RC, et al. "Material Differentiation by Dual Energy CT: Initial Experience" European Radiology, 2007, 17, pp. 1510-1517.

*Primary Examiner* — Van D Huynh
(74) *Attorney, Agent, or Firm* — Canon U.S.A., Inc. IP Division

(57) ABSTRACT

A medical image processing apparatus acquires a plurality of medical images obtained by imaging an identical region of an object under different radiographing conditions, acquires a correlation between a signal value and a radiographing condition at a pixel at a same position in the plurality of medical images, acquires a virtual radiographing condition that is different from the radiographing conditions of the plurality of medical images, generates an image for a diagnosis by acquiring a signal value of each pixel based on the correlation and the virtual radiographing condition, and acquires a window width value and a window level value for displaying one medical image of an identical cross section of the object.

14 Claims, 14 Drawing Sheets

(51) Int. Cl.
  *A61B 6/00*     (2006.01)
  *G06T 5/00*     (2006.01)
  *G06T 11/00*    (2006.01)
(52) U.S. Cl.
  CPC .......... *G06T 11/003* (2013.01); *G06T 11/008* (2013.01); *G06T 2207/10081* (2013.01); *G06T 2207/10088* (2013.01); *G06T 2207/20092* (2013.01)
(58) Field of Classification Search
  CPC ......... G06T 2207/10116; A61B 6/5294; A61B 6/032; A61B 6/5217
  USPC ................................................ 382/131, 132
  See application file for complete search history.

(56) References Cited

U.S. PATENT DOCUMENTS

| | | | |
|---|---|---|---|
| 2006/0241402 A1* | 10/2006 | Ichihara | ................. A61B 6/481 600/425 |
| 2011/0280456 A1 | 11/2011 | Sussman et al. | |
| 2012/0189183 A1 | 7/2012 | Xue et al. | |
| 2012/0263361 A1 | 10/2012 | Boettger et al. | |
| 2015/0193932 A1* | 7/2015 | Hashimoto | ............ A61B 6/032 382/132 |
| 2016/0073994 A1* | 3/2016 | Fujisawa | .............. A61B 6/5217 382/131 |
| 2016/0217585 A1* | 7/2016 | Yoshida | ................... G06T 5/50 |

FOREIGN PATENT DOCUMENTS

| | | | |
|---|---|---|---|
| JP | 62-189055 A | 8/1987 | |
| JP | 63-298279 A | 12/1988 | |
| WO | 2015/162694 A1 | 10/2015 | |

\* cited by examiner

WINDOW WIDTH VALUE 300, WINDOW LEVEL VALUE 30

WINDOW WIDTH VALUE 300, WINDOW LEVEL VALUE 30

WINDOW WIDTH VALUE 120, WINDOW LEVEL VALUE 60

WINDOW WIDTH VALUE 2344, WINDOW LEVEL VALUE 807

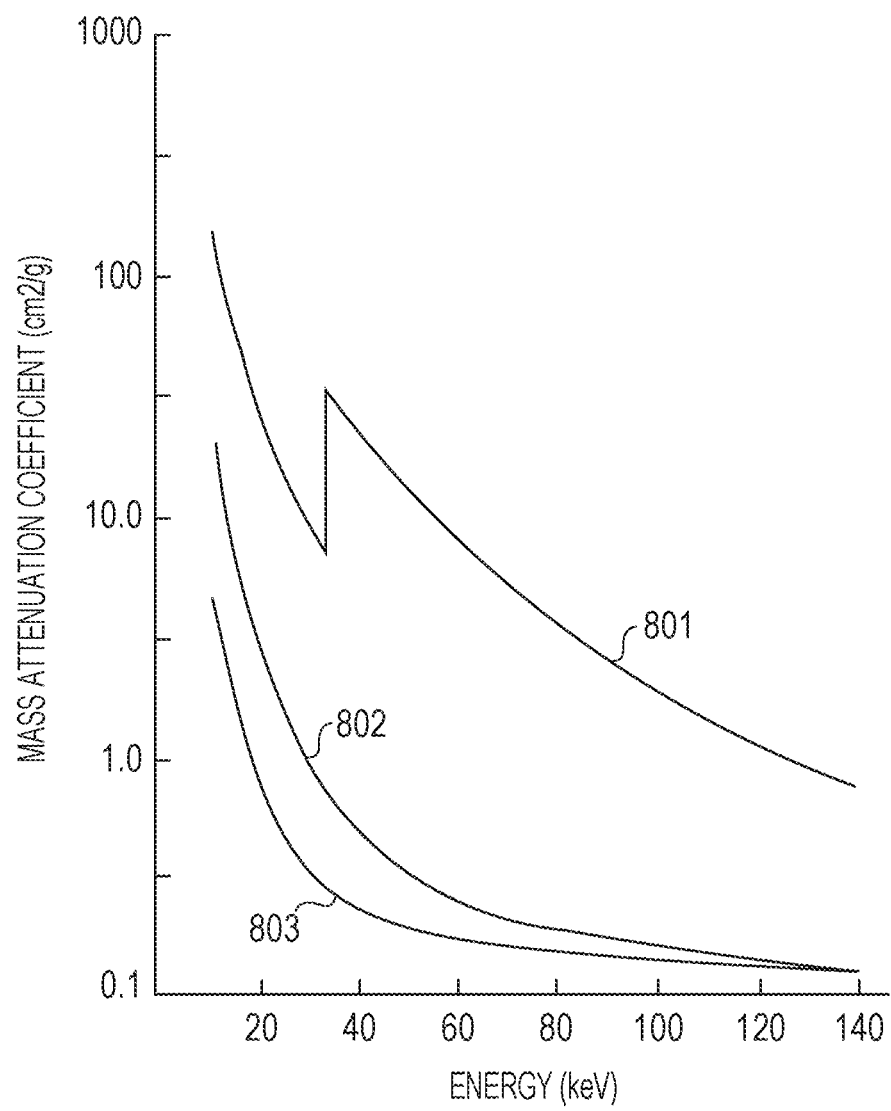

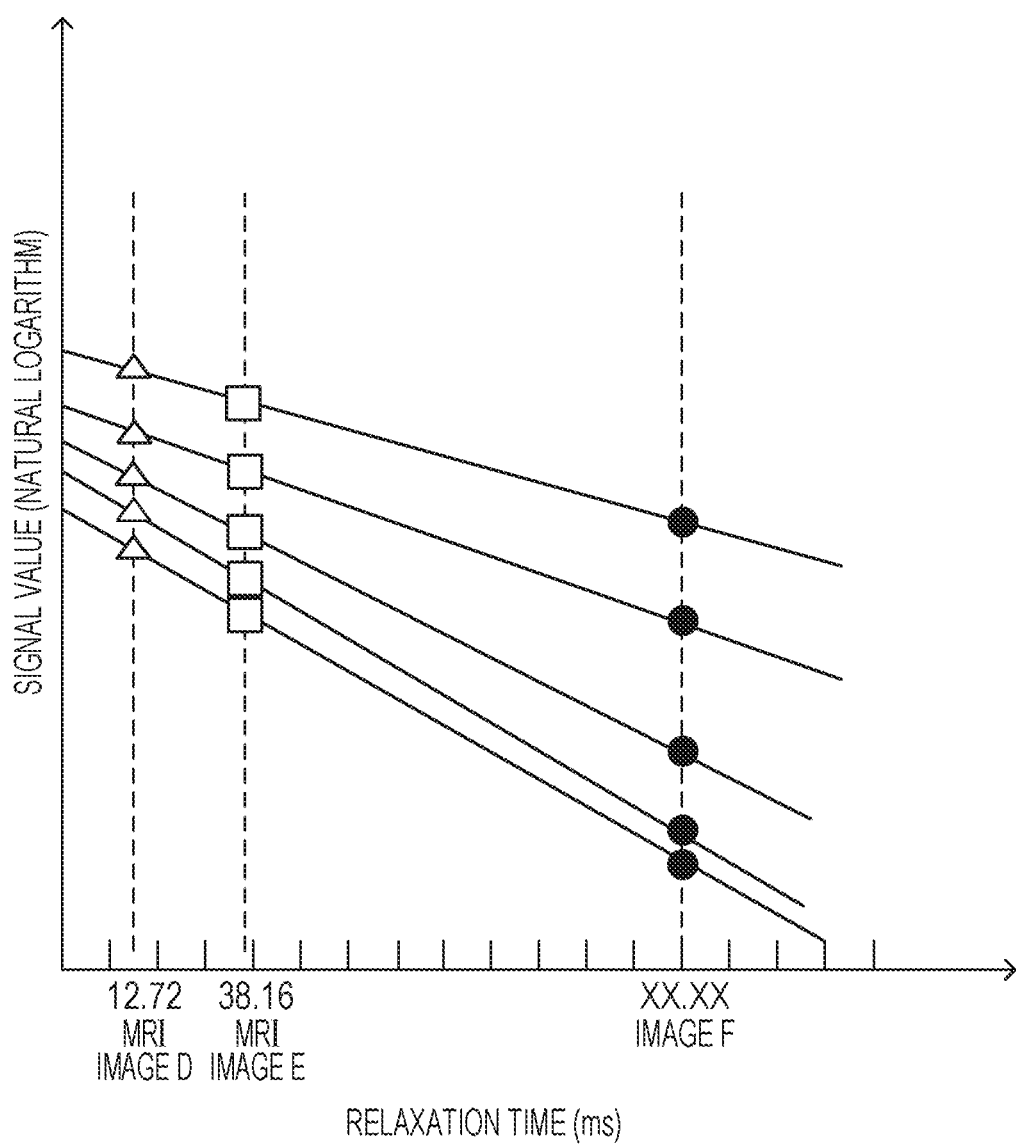

WW/WL = 6000/2000

WW/WL = 1283/3 ized to the US 10,002,423 B2

MEDICAL IMAGE PROCESSING APPARATUS, MEDICAL IMAGE PROCESSING METHOD, AND MEDICAL IMAGE PROCESSING SYSTEM

BACKGROUND OF THE INVENTION

Field of the Invention

The present invention relates to a medical image processing apparatus, and a medical image processing method.

Description of the Related Art

Recently, various kinds of medical image capturing apparatus have been used, and medical images captured under radiographing conditions in accordance with given purposes have been used for diagnoses. For example, Johnson, Thorsen R C, et al., "Material differentiation by dual energy CT: initial experience", European radiology 17.6 (2007): 1510-1517, discloses a technology including comparing computed tomography (CT) values of two data sets captured with different X-ray tube voltages and estimating an existence probability of iodine in each pixel to change a CT image to an iodine concentration map (iodine map). U.S. Pat. No. 5,655,532 discloses a technology including imaging by changing the lengths of time periods for acquiring signals to acquire an enhanced image by enhancing a specific component by using a longitudinal relaxation phenomenon and a transverse relaxation phenomenon.

SUMMARY OF THE INVENTION

According to some embodiments of the present invention, a medical image processing apparatus includes an image acquiring unit configured to acquire a plurality of medical images obtained by imaging an identical region of an object under different radiographing conditions, a relation acquiring unit configured to acquire a correlation between a signal value and a radiographing condition at a pixel at a position mutually corresponding in the plurality of medical images, a condition acquiring unit configured to acquire a virtual radiographing condition that is different from the radiographing conditions of the plurality of medical images, a generating unit configured to generate a diagnosis image by acquiring a signal value of each pixel based on the correlation and the virtual radiographing condition, a display condition acquiring unit configured to acquire a window width value and a window level value for displaying one medical image of an identical cross section of the object, and a display control unit configured to cause a display unit to display the diagnosis image based on the window width value and window level value acquired by the display condition acquiring unit.

Further features of the present invention will become apparent from the following description of exemplary embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

BRIEF DESCRIPTION OF THE DRAWINGS

FIG. 8 illustrates a relation between X-ray energy and mass attenuation coefficients of a contrast agent and a bone and muscles.

FIG. 13 illustrates a method for identifying a signal value of a pixel at a virtual relaxation time designated by a user from a relation between signal values of pixels of two MRI images and radiographing conditions according to the second exemplary embodiment.

DESCRIPTION OF THE EMBODIMENTS

First Exemplary Embodiment

Figure 1A:
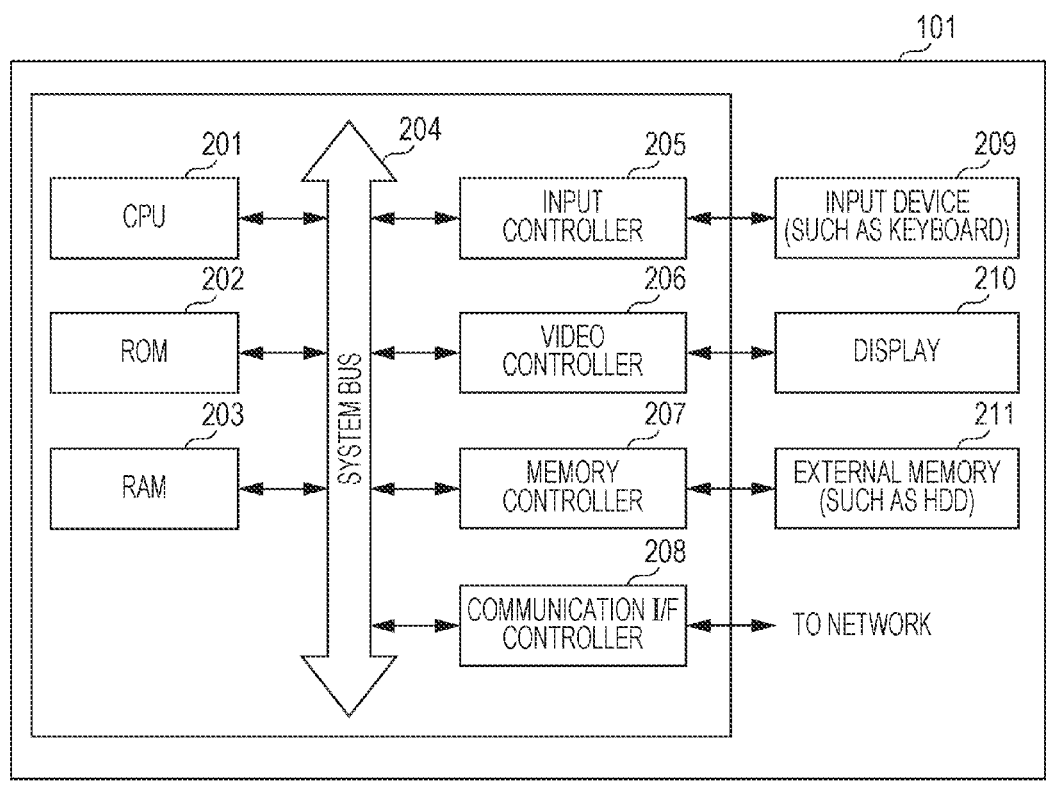
FIGS. 1A and 1B illustrate a hardware configuration and a functional configuration of a medical image processing apparatus.

An X-ray CT apparatus reconstructs information acquired by projecting to an object an X-ray from an X-ray tube which rotates around the object based on parameters such as a predetermined X-ray tube voltage and X-ray tube current to image an internal part of the object.

A typical X-ray CT apparatus replaces a CT value used as a substance inherent value by a gray scale and displays it on a viewer so that radiogram interpretation can be performed for detecting a lesion, for example. Such a CT value may be acquired by normalizing a "linear attenuation coefficient" that is a value associated with an atomic number or density of a substance by using a linear attenuation coefficient of water. The linear attenuation coefficient has a characteristic dependent on the X-ray tube voltage being the intensity of an X-ray for computed tomographic (CT) imaging.

Therefore, the CT value depends on the X-ray tube voltage. In order to acquire reproducibility for normal medical radiogram interpretation, an image captured by using 120-kV X-ray tube voltage is often used in general.

In recent years, on the other hand, a technology or an imaging method which uses a change in CT value due to such X-ray tube voltage to extract a specific substance only has emerged. The technology is called Dual Energy CT. According to the imaging method, two data sets captured with 80 kV and 140 kV are used to compare their CT values and thus selectively extract a specific substance based on the amount of change in accordance with the atomic number of the substance.

It is known that the amount of change in mass attenuation coefficient is larger when X-ray energy is changed, as illustrated in FIG. 8, because iodine 801 used as a contrast agent for computed tomographic (CT) imaging has a higher atomic number than those of organic compounds (bone 802 and muscles 803) included in the body of an object.

Because of that, CT values of two data sets captured with different X-ray tube voltages are compared to estimate an existence probability of iodine in each pixel. Thus, the CT image can be changed to an iodine concentration map (iodine map). This iodine map can enhance iodine taken into a tissue for display, which is effective for identifying a region in which a blood flow is blocked by an infraction or an Angiogenesis due to a carcinogenesis. In other words, an image captured by Dual Energy CT may be used to distinguish between a normal region and an abnormal region within the tissue.

However, even when such an iodine map is used which enhances intake of iodine for display, it is concerned that an abnormal region may not be identified easily due to a partial volume effect in a case where a cancer cell is minute in an object tissue or the efficiency of intake of a contrast agent is low in the tissue.

Accordingly, a medical image processing apparatus according to a first exemplary embodiment allows a user to instruct to display an image from which an abnormal region such as a cancer cell can be identified easily even in a case where the abnormal region is minute or the efficiency of intake of a contrast agent is low.

The first exemplary embodiment uses two CT images (medical images) captured by Dual Energy CT with 80 kV and 140 kV by administering a contrast agent such as iodine to a patient (object) laid on a bed. The two medical images can be acquired by Dual Energy CT by irradiating X-rays to an identical object (patient) at substantially equal times with high and low X-ray tube voltages, which are different voltages from each other, by an X-ray CT apparatus between a high voltage and a low voltage.

The 256 gradation gray scale is used for displaying such CT images captured by an X-ray CT apparatus on a display device in a medical image processing apparatus, for example. A CT value represents a relative value of an X-ray attenuation rate of a substance by defining the X-ray attenuation rate of water as 0 HU and the X-ray attenuation rate of the air as −1000. Thus, a CT value acquired by imaging the body varies in a range from about −100 HU to 3000 HU.

The gray scale used for displaying such a CT image is associated with CT values. However, full correspondence between a whole range of the CT values and a whole range of the gray scale may prevent enhancement of a desired tissue for checking. Because of the problem, the correspondence relation between CT values and the gray scale is generally defined as a window width value (WW) and a window level value (WL), and the whole range or a partial range of the gray scale may be associated with a necessary range of CT values to display the desired display result.

The term "window level value" here refers to a CT value being a center for display in gray scale, and the term "window width value" refers to a range to be displayed in gray scale. More specifically, when the window width value is equal to 300 and the window level value is equal to 30, the center CT value is equal to 30, and a width of 150 with 30 at its center is a range of the CT value to be displayed in other words, CT values from −120 to 180 correspond to a CT value range to be observed, and a gray scale from 0 to 255 is associated the CT value range for display on a display device.

FIG. 1A illustrates a hardware configuration example of a medical image processing apparatus 101 according to a first exemplary embodiment. The medical image processing apparatus 101 according to the first exemplary embodiment acquires (or loads) volume data captured by a medical image diagnosis apparatus such as a CT apparatus from a storage device storing the volume data and performs an image process.

A CPU 201 generally controls devices and controllers connected to a system bus 204.

A ROM 202 or an external memory 211 (storage unit) stores a BIOS (Basic Input/Output System) and an operating system program (hereinafter, called an OS) which are control programs for the CPU 201 and programs, which will be described below, for implementing functions executed by the medical image processing apparatus 101. A. RAM 203 functions as a main memory and a work area, for example, for the CPU 201.

The CPU 201 loads a program for execution of processing to the RAM 203 and executes the program to implement an operation.

An input controller (or input C) 205 controls an input through an input device 209 such as a keyboard and a pointing device such as a mouse, not illustrated.

A video controller (VC) 206 controls display to a display device such as a display device 210. The type of display device is assumed to be, but not being limited to, a CRT or a liquid crystal display.

A memory controller (MC) 207 controls accesses to the external memory 211 storing a boot program, browser software, applications, font data, user files, edit files, and data, such as a hard disk (HD), a flexible disk (FD) or a card type memory connected to a PCMCIA card slot through an adapter.

A communication interface (I/F) controller (communication I/FC) 208 is communicatively connected, over a network, with an external apparatus such as a storage device storing an image acquired by a medical image diagnosis apparatus such as a CT apparatus and executes communication control processing over the network. For example, the communication. I/FC 208 enables Internet communication based on TCP/IP.

The CPU 201 may execute processing for decompressing (or rasterizing) an outline font to a display information region within the RAM 203, for example, to enable it to be displayed on the display device 210.

The CPU 201 enables a user to instruct, by using a mouse cursor, not illustrated, on the display device 210.

Programs to be used for executing processes, which will be described, by the medical mace processing apparatus 101 according to the first exemplary embodiment are stored in the external memory 211, are loaded to the RAM 203 as required, and are executed by the CPU 201.

Definition files and information tables used by the programs according to the first exemplary embodiment are stored in the external memory 211.

Figure 1B:
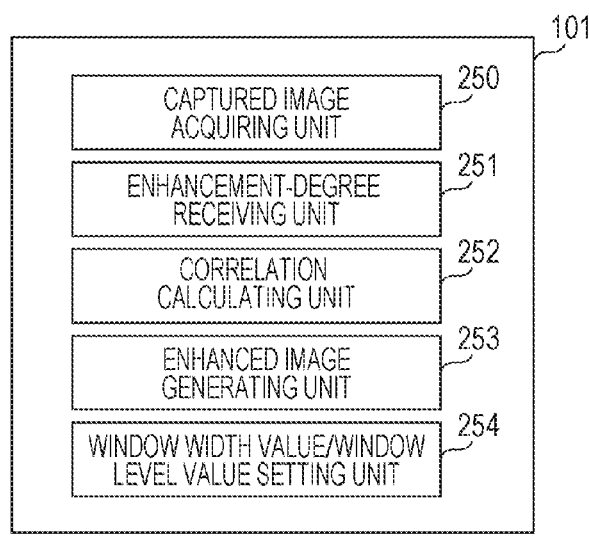

FIG. 1B illustrates a functional configuration of the medical image processing apparatus 101. The CPU 201 in the medical image processing apparatus 101 functions as a captured image acquiring unit 250, an enhancement-degree receiving unit 251, a correlation calculating unit 252, an enhanced image generation unit 253, and a window width value/window level value setting unit 254.

The captured image acquiring unit 250 acquires two-dimensional images corresponding to an identical position (or an identical cross section) from a plurality of medical images (volume data sets) captured with mutually different X-ray tube voltages by a medical image diagnosis apparatus such as a CT apparatus.

The enhancement-degree receiving unit 251 is configured to receive from a user an enhancement degree for a contrast agent desired by the user through, for example, a screen displayed on a display device. According to the first exemplary embodiment, a virtual X-ray tube voltage is designated by a user as the enhancement degree. An embodiment of the present invention is not limited thereto, but it may only be required to receive an enhancement degree desired by a user.

The correlation calculating unit 252 acquires a correlation between a CT value and an X-ray tube voltage at a pixel at identical coordinates in a two-dimensional image included in a plurality of volume data sets captured with mutually different X-ray tube voltages. In this case, the correlation may be calculated for all pixels within a medical image, but correlations may be calculated only for pixels having predetermined or higher signals.

The enhanced image generation unit 253 identifies a CT value for each pixel with an enhancement degree designated by a user based on the correlation and generates an enhanced image by using the CT values.

The window width value/window level value setting unit 254 sets a window width value (WW)/window level value (WL) for displaying the enhanced image.

Figure 2:
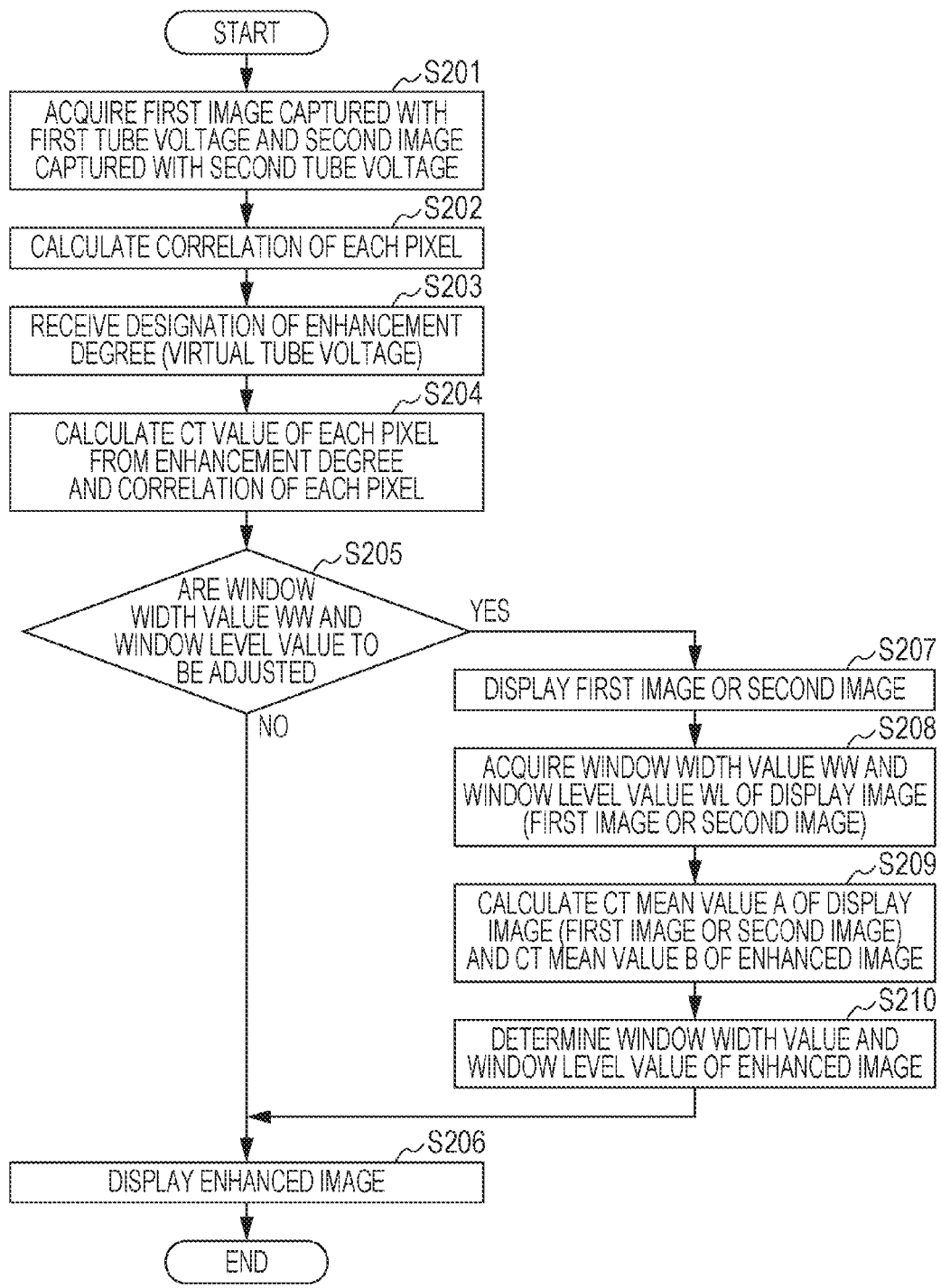
FIG. 2 is a flowchart illustrating a flow of processing according to a first exemplary embodiment.

FIG. 2 is a flowchart illustrating a flow of medical image processing to be performed by the medical image processing apparatus 101 according to the first exemplary embodiment. The processing illustrated in the flowchart in FIG. 2 is implemented by a stored control program read out and executed by the CPU 201 in the medical image processing apparatus 101.

A user first performs processing for reading out a desired volume data set. More specifically, the CPU 201 in the medical image processing apparatus 101 acquires CT image data corresponding to an image designated by a user acquired by a medical image diagnosis apparatus such as a CT apparatus from an external storage device (not illustrated) provided communicatively. The CT image data acquired here include at least two volume data sets acquired by capturing one object with mutually different X-ray tube voltages at substantially same times, and each of the volume data sets (three-dimensional medical image data sets) includes a plurality of slice images (two-dimensional images). The thus acquired volume data sets are stored in a storage unit (external memory or a RAM) of the medical image processing apparatus 101.

Figure 4B:
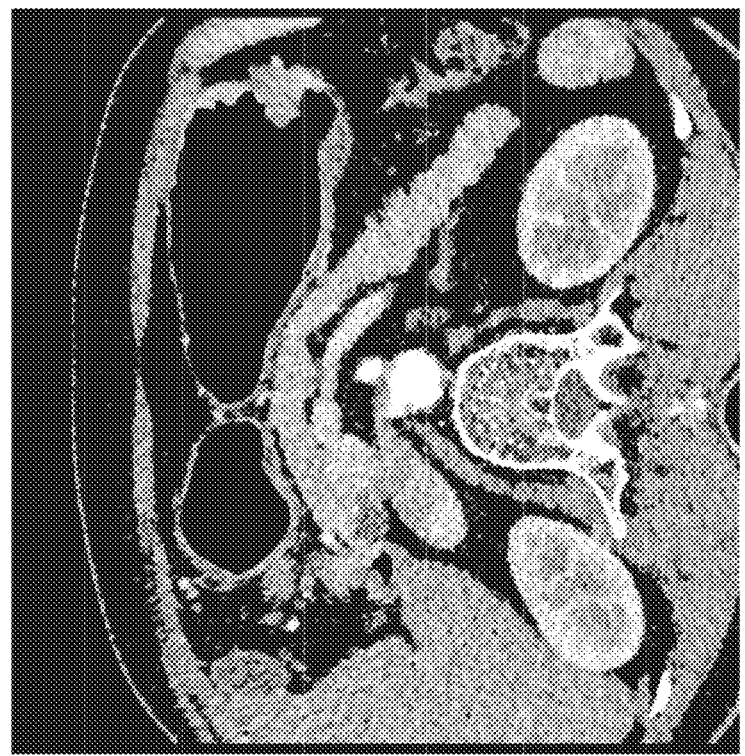
FIG. 4B illustrates an example image captured with 140 kV X-ray tube voltage.
Figure 4A:
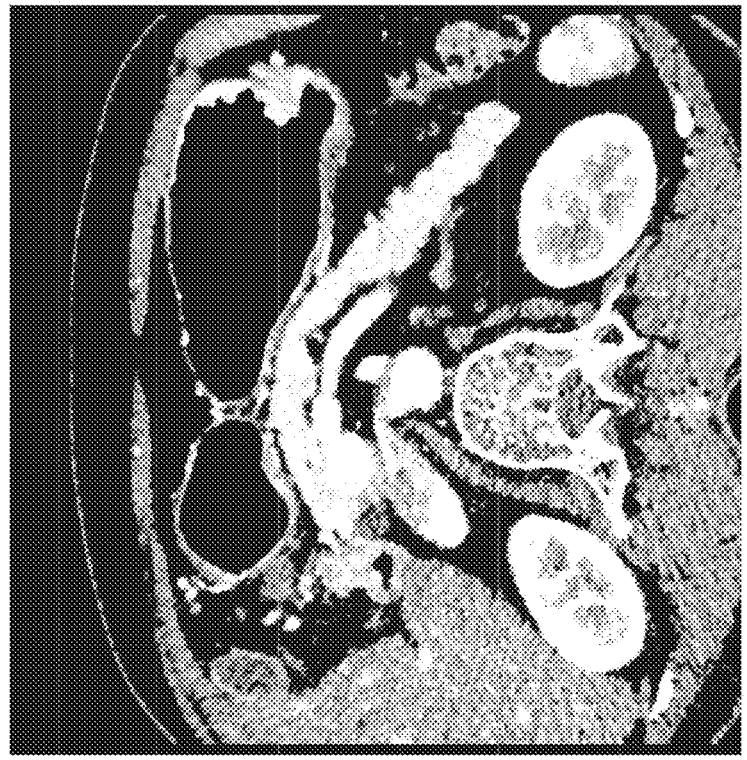
FIG. 4A illustrates an example image captured with 80 kV X-ray tube voltage.

In step S201, the CPU 201 in the medical image processing apparatus 101 acquires two two-dimensional images captured with mutually different X-ray tube voltages and corresponding to an identical position (identical cross section) designated by a user from the volume data. The two-dimensional images acquired here may be cross sections acquired by taking volume data at an arbitrary plane. In the first exemplary embodiment, a CT image A captured with 80 kV, which is illustrated in FIG. 4A, and a CT image B captured with 140 kV, which is illustrated in FIG. 4B, are acquired for illustration purpose.

Figure 5:
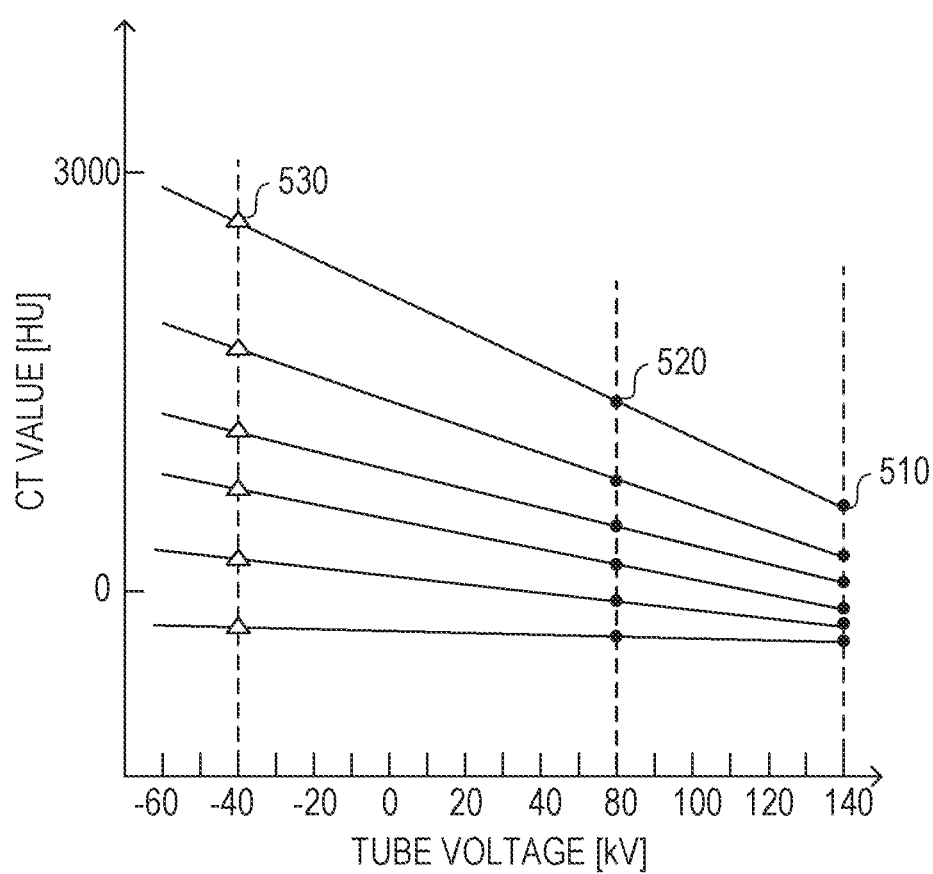
FIG. 5 illustrates how a CT value is determined with a desired virtual X-ray tube voltage based on a relation between X-ray tube voltage and CT values of two medical images.

In step S202, the CPU 201 in the medical image processing apparatus 101 acquires a correlation between a CT value of a pixel and the X-ray tube voltages at identical coordinates of the two two-dimensional images acquired in step S201. FIG. 5 illustrates a correlation of a pixel at identical coordinates having a CT value of 520 in the CT image A captured with 80 kV and a CT value of 510 in the CT image B captured with 140 kV. The CT values at two points are used for the approximation for the correlation between X-ray tube voltage and the CT value. FIG. 5 illustrates an example of a linear approximation of a correlation between pixels at identical coordinates by using CT values at two points. The amount of change in CT value of a pixel strongly influenced by iodine, for example, is larger than the amount of changing CT value of a pixel not influenced by iodine, for example. The correlation to be acquired in step S202 may be calculated for all pixels within a medical image but may be calculated only for pixels having a predetermined signal value or higher.

Figure 3A:
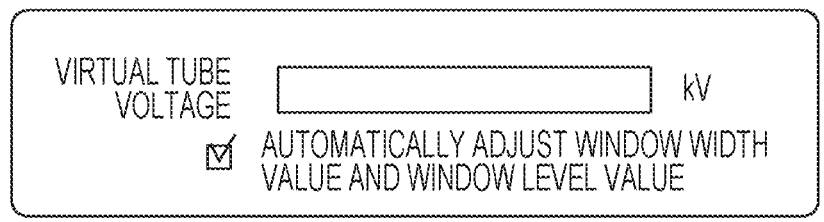
FIGS. 3A and 3B illustrate screen examples usable by a user for designating an enhancement degree (virtual X-ray tube voltage).
Figure 3B:
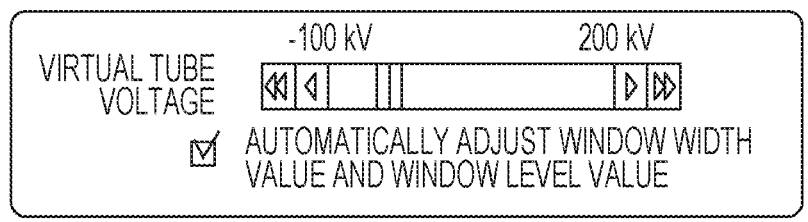

In step S203, the CPU 201 in the medical image processing apparatus 101 receives a designated enhancement degree from a user. The enhancement degree may be designated as a virtual X-ray tube voltage, for example, through a virtual X-ray tube voltage value input screen displayed on a display device as illustrated in FIG. 3A or through an input screen with a slide bar as illustrated in FIG. 3B, which may be changed in real time. The enhancement degree may be input not only as a virtual X-ray tube voltage but also as an enhancement rate for enhancing a pixel having a larger amount of change in CT value between the CT image A and the CT image B. From a different point of view, the CPU 201 in the medical image processing apparatus 101 in S203 receives a virtual radiographing condition from a user. The virtual X-ray tube voltage is an example of the virtual radiographing condition.

In step S204, the CPU 201 in the medical image processing apparatus 101 acquires a CT value of each pixel having the enhancement degree designated by the user in step S203 from the correlation of the pixels at identical coordinates calculated in step S202. More specifically, in a case where a virtual X-ray tube voltage of −40 kV is received as an enhancement degree designated by a user, a CT value 530 at identical coordinates to those of the pixel assumed to be acquired by being captured with −40 kV is acquired from the linear approximation curve acquired from the pixel at identical coordinates illustrated in FIG. 5. This processing may be performed on all pixels to acquire a CT value of the enhanced image C. In a case where correlations are acquired for pixels having a predetermined signal value or higher in step S202, CT values for coordinate positions of the pixels may be calculated. The enhanced image C is an example of an image for a diagnosis (hereinafter, called a diagnosis image).

In step S205, the CPU 201 in the medical image processing apparatus 101 determines whether the window width value WW and window level value WL for displaying the enhanced image C are to be automatically adjusted. More specifically, it may be determined based on conditions selected by a user on the screen as illustrated in FIGS. 3A and 3B. If a user designates to automatically adjust them, the processing moves to step S207. If not, the processing moves to step S206. The determination in step S205 is not required in the first exemplary embodiment, and the processing map move to step S207 to step S210 and subsequent steps without performing the determination or may move to step S206 without performing the processing in step S207 to step S210.

In step S206, the CPU 201 in the medical image processing apparatus 101 performs display control for displaying an enhanced image C' with an arbitrary window width value WW and an arbitrary window level value WL.

Figure 6A:
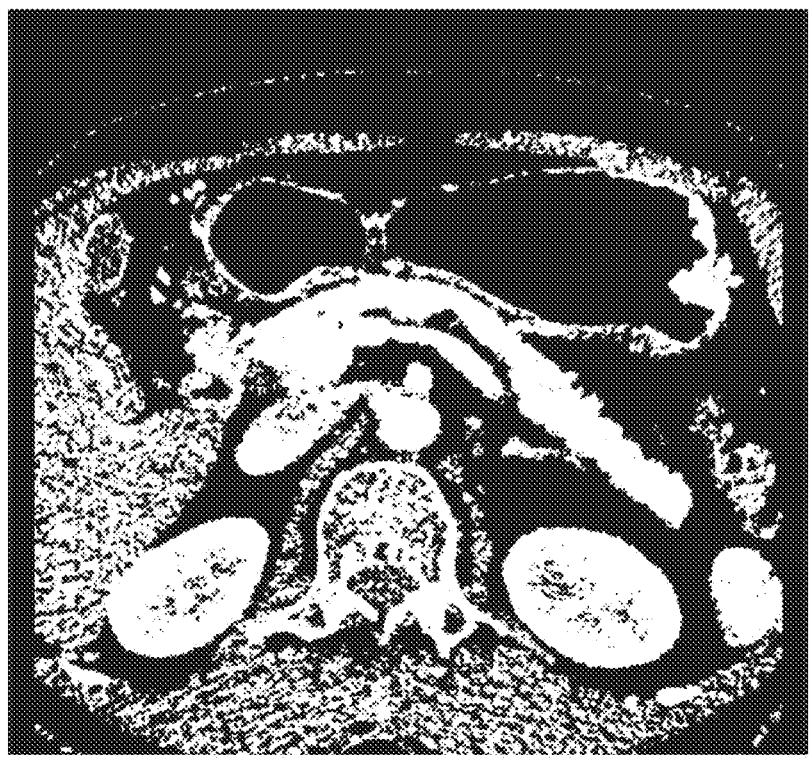
FIG. 6A illustrates an example enhanced image with −40 kV virtual X-ray tube voltage.
Figure 6B:
FIG. 6B illustrates an enhanced image acquired by adjusting a window level value and a window width value of the enhanced image in FIG. 6A by a user.

FIG. 6A illustrates an example of the enhanced image C generated and displayed as described above. A user may adjust the window width value WW and window level value WL of the image in FIG. 6A to acquire the enhanced image C' as illustrated in FIG. 6B. FIG. 6B illustrates a region 601 partially having a high CT value from which it is found that a minute gastric cancer exists there. Under a condition where the window width value WW and window level value WL of the enhanced image are appropriate, a state indicated by the CT values which are not easily identified from the original CT image A and CT image B illustrated in FIGS. 4A and 4B can be displayed in an enhanced manner. In other words, even when an abnormal region such as a cancer cell is minute (small) or when the given tissue takes in less of a contrast agent, a user can easily identify the abnormal region in the resulting image.

In S207, the CPU 201 in the medical image processing apparatus 101 displays the CT image A captured with 80 kV or the CT image B captured with 140 kV and prompts a user to set the window width value WW and window level value WL for displaying the image. The image to be used for setting the window width value WW and window level value WL by a user may be any CT image of the same cross section of the same patient, rather than the CT image A and the CT image B.

Figure 7A:
FIG. 7A illustrates a medical image captured with 80 kV X-ray tube voltage acquired by adjusting a window level value and a window width value by a user.

In step S208, the CPU 201 in the medical image processing apparatus 101 acquires the window width value WW and window level value WL set by a user for the medical image displayed in step S207 (display condition acquiring unit). FIG. 7A illustrates a CT image A' after a user adjusts the CT image. A captured with 80 kV X-ray tube voltage by the user by applying a window width value WW and a window level value WL for clear display. In step S208, window width value WW: 120 and window level value WL: 60 are acquired.

In step S209, the CPU 201 in the medical image processing apparatus 101 acquires a CT mean value K of the CT image A' displayed in step S207 and a CT mean value L of the enhanced image C calculated in step S205 (mean value calculating unit). Mean values for all pixels are not required here, but use of an identical pixel may only be required for acquiring the CT mean value K and the CT mean value L. Thus, for example, the CT mean value K and CT mean value L may correspond to pixels having a predetermined CT value or higher in the CT image displayed in step S207, or the CT mean value K and CT mean value L may correspond to pixels having a predetermined CT value or higher in the enhanced image C.

In step S210, the CPU 201 in the medical image processing apparatus 101 uses the window width value and window level value acquired in step S208 and the CT mean value K and CT mean value L calculated in step S209 to determine the window width value WW and window level value WL to be used for displaying the enhanced image C on a display device. More specifically, the window width value WW to be used for displaying the enhanced image C are determined by multiplying the window width value WW acquired in step 1208 by CT mean value L/CT mean value K acquired by dividing the CT mean value L by the CT mean value K. The window level value WL to be used for displaying the enhanced image C on the display device is determined by multiplying the window level value WL acquired in step S208 by CT mean value L/CT mean value K acquired by dividing the CT mean value L by the CT mean value K.

After that, the processing moves to step S206 where display control is executed such that the enhanced image can be displayed with the window width value WW and window level value WL determined in step S210. The automatic determination of the window width value WW and window level value WL can reduce user's work for adjustment.

Figure 7B:
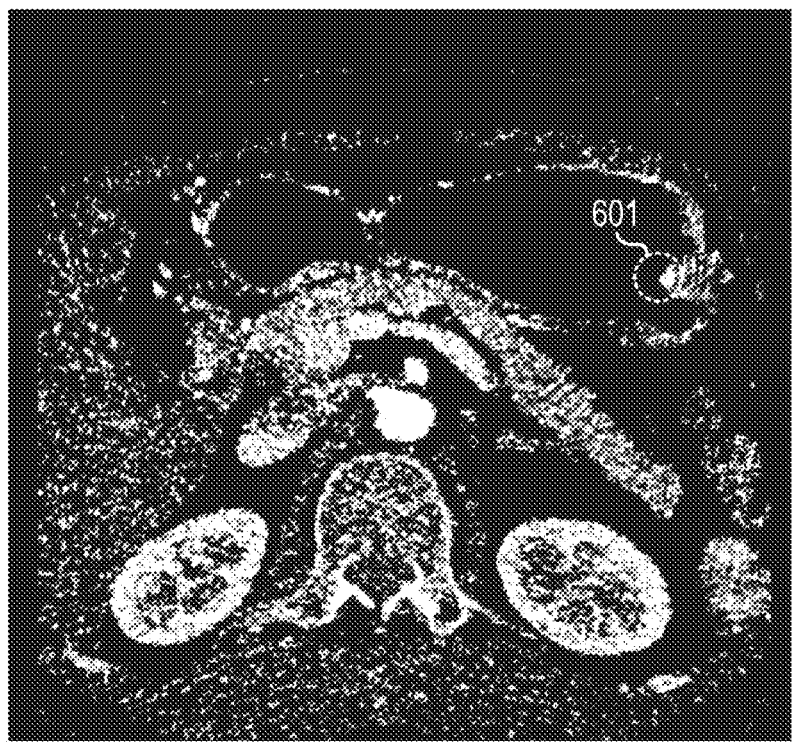
FIG. 7B is a medical image acquired by setting a window level value and a window width value in accordance with the window level value and window width value set for the medical image in FIG. 7A.

FIG. 7B illustrates an enhanced image C'' acquired by setting to the window width value WW and window level value WL determined by using the window width value WW and window level value WL in FIG. 7A and the CT mean value K of the image and the CT mean value L of the enhanced image C illustrated in FIG. 7A. Thus, through the automatic setting of the window width value WW and window level value WL, an enhanced image can be displayed from which it can be determined that a minute gastric cancer exists in the region 601, eliminating the necessity for a user to adjust the window width value WW and window level value WL. A changed state of the CT values which is not easily identified from the original CT image A and CT image B illustrated in FIGS. 4A and 4B can be displayed in an enhanced manner. Even when an abnormal region such as a cancer cell is minute or when the given tissue takes in less of a contrast agent, a user can easily identify the abnormal region in the resulting image.

According to the first exemplary embodiment as described above, an enhanced image of two-dimensional images is acquired by using pixels of the two-dimensional images. The same is true for voxels to generate an enhanced image. In other words, a correlation may be acquired for voxels at identical coordinates on three-dimensional medical images, and a CT value of the voxel with a virtual X-ray tube voltage can be acquired based on the correlation to generate an enhanced image thereof.

Having described that, according to the first exemplary embodiment, two medical images captured with 80 kV and 140-kV substantially at the same time to acquire a correlation, medical images captured with other X-ray tube voltages may be used to acquire a correlation, or medical images captured substantially at the same time may not be used. Three or more medical images captured with mutually different X-ray tube voltages may be used to acquire a correlation. The correlation may be not only a function acquired by linear approximation but also a function acquired by exponential approximation, logarithmic approximation, polynomial approximation, moving averaging.

Having described that, according to the first exemplary embodiment, both of the window width value (WW) and the window level value (W) are adjusted, only one of them may be adjusted.

In the medical image processing apparatus according to the first exemplary embodiment as described above, a plurality of medical images captured with mutually different X-ray tube voltages and an enhancement degree designated by a user are used to generate and display an enhanced image. Thus, an image from which an abnormal region can be identified easily by a user can be obtained even in a case where the abnormal region is minute or the efficiency of intake of a contrast agent is low.

Second Exemplary Embodiment

MRI (magnetic resonance imaging) performs a magnetic operation on protons of a biological tissue to acquire its signal intensity depending on the tissue of the body. Thus, the signal intensity may be used to perform diagnostic imaging on the body.

In general, an MRI apparatus may be used to project electromagnetic waves (RF pulses) which tilt the axis of rotation of protons by 90° to an object placed within a static magnetic field to apply energy to the protons and then stop the irradiation of the electromagnetic waves. Thus, the protons return to a stationary state while emitting energy. The energy emission state (relaxation state) at that time may be used to acquire an image. As the relaxation state, there are two types of relaxation phenomena: a longitudinal relaxation phenomenon (T1 relaxation) and a transverse relaxation phenomenon (T2 relaxation). A T1 value being a time constant in the longitudinal relaxation phenomenon corresponds to a time period necessary for a signal to recover to the initial 63%, and a T2 value being a time constant in the transverse relaxation phenomenon corresponds to a time period necessary for a signal to attenuate to the initial 37%. These values vary among molecules.

In other words, such a relaxation phenomenon is a signal change with a lapse of time. For example, water molecules have a low degree of signal attenuation in the transverse relaxation phenomenon. Thus, use of signals acquired over a sufficiently long period of time can provide an image having water molecules enhanced because signals other than the signals of water molecules can completely attenuate. Such an image showing a specific component in a tissue in an enhanced manner by using the longitudinal relaxation phenomenon or the transverse relaxation phenomenon is called an "enhanced image". An image enhanced by using a longitudinal relaxation is called a T1 enhanced image, and an image enhanced by using a lateral relaxation is called a T2 enhanced image. A method has been known which captures such an enhanced image by using an MRI apparatus.

A radiologist, for example, may use a previously captured MRI image for X-ray interpretation. However, such an image may not have a difference in relaxation desired by a radiologist in an object tissue, and the radiologist may not make a correct diagnosis in some cases. In order for a radiologist to make a reliable diagnosis in such a case, capturing an MRI image having an enhanced difference in relaxation in an object tissue may be required by changing a radiographing condition such as a relaxation time in an MRI apparatus.

However, capturing a patient again by changing a radiographing condition in the MRI apparatus may undesirably take a long time and much effort.

Accordingly, in the medical image processing apparatus according to the second exemplary embodiment, a mechanism may be provided which can provide a radiogram interpretation image showing an object tissue in an enhanced manner without capturing an image of the object again by using the MRI apparatus.

The medical image processing apparatus 101 illustrated in FIGS. 1A and 1B may store in the external memory 211 three-dimensional image data (volume data) of a patient (object) captured by a magnetic resonance imaging apparatus (MRI apparatus) and display an MRI image of a desired cross section. Having described that, according to the second exemplary embodiment, three-dimensional image data are stored in the external memory 211 in the medical image processing apparatus 101, the image data may be stored in an image server connected communicatively to the medical image processing apparatus 101.

The MRI image applied in the second exemplary embodiment is a T2 enhanced image being an image having a signal value acquired by using a lateral relaxation, for example. Electromagnetic waves (RF pulses) may be projected to a patient laid on a bed to tilt the axis of rotation of protons by 90° and thus add energy to the protons so that the projected added energy can be received. Because the composition of contained molecules being protons may vary in accordance with the tissue containing the molecules, the degree of energy projection may vary. Energy may attenuate quickly in one tissue while energy may attenuate in a long period of time in another tissue. Therefore, a lapse time (hereinafter, called a relaxation time) from a termination of projection of electromagnetic waves (RF pulses) to imaging may be changed to acquire an image showing a desired tissue with an enhanced signal value. The term, T2 enhanced image, refers to an image captured when the moisture state of molecules can be grasped and showing moisture in a more enhanced manner than other molecules because of an influence of a lateral relaxation.

Two MRI images used in one second exemplary embodiment are T2 enhanced images captured at mutually different relaxation times and are medical images acquired by capturing one object (patient) at substantially same times. According to the second exemplary embodiment, a correlation between signal value and relaxation time is acquired for each pixel from the two MRI images. However, an embodiment of the present invention may use two or more MRI images. The MRI images to be used for acquiring the correlation may not be T2 enhanced images enhancing an influence of a lateral relaxation but may be T1 enhanced images enhancing a specific tissue with a difference in longitudinal relaxation. Here, the term "T1 enhanced image" refers to an image showing fat in a more enhanced manner because of an influence of a longitudinal relaxation than other molecules such as water and captured when the fat state can be grasped. A T1 enhanced image may be an MRI image captured by a STIR method or a FLAIR method plurality of MRI images to be used for acquiring the correlation may only be required to be associated with an identical type of relaxation. Thus, at least two T2 enhanced images are required to generate a T2 virtual enhanced image by changing the relaxation time for the T2 enhanced images. At least two T1 enhanced images are required to generate a T1 virtual enhanced image by changing the relaxation time for the T1 enhanced images.

The gray scale to be used for displaying such. MRI images corresponds to signal values. However, when a whole range of the signal values and a whole range of the gray scale completely correspond to each other, a desired tissue may not be enhanced for checking. Against the problem, a correspondence relation between signal value and gray scale may be defined as a window width value (WW) and a window level value (WL), and all or a partial range of gray scale is associated with a desired range of signal values in general so that a desired display result can be displayed.

The term "window level value" here refers to a signal value being a center for displaying an image on gray scale, and the term "window width value" refers to a range for shading display. More specifically, when the window width value is equal to 6000 and the window level value is 2000, the center signal value is equal to 2000, and a width of 6000 about 2000 as the center signal value is a range of signal values to be displayed. In other words, signal values from −4000 to 8000 fall within a range of signal values to be observed, and gray scale levels 0 to 255 are associated with the signal values in the range for display on the display device 210.

Because the hardware configuration of the medical image processing apparatus 101 according to the second exemplary embodiment is the same as the one illustrated in FIG. 1, the aforementioned descriptions are applied, and repetitive detail descriptions will be omitted. The hardware configuration of the medical image processing apparatus 101 in FIG. 1 is given for illustration purpose only and may vary in accordance with usages and purposes.

Programs to be used for executing processes, which will be described below, by the medical image processing apparatus 101 according to the second exemplary embodiment are stored in the external memory 211 and are loaded to a. RAM 202 so that the CPU 201 can execute them. Definition files, information tables, and MRI images to be used by programs according to the second exemplary embodiment are stored in the external memory 211.

Figure 9:
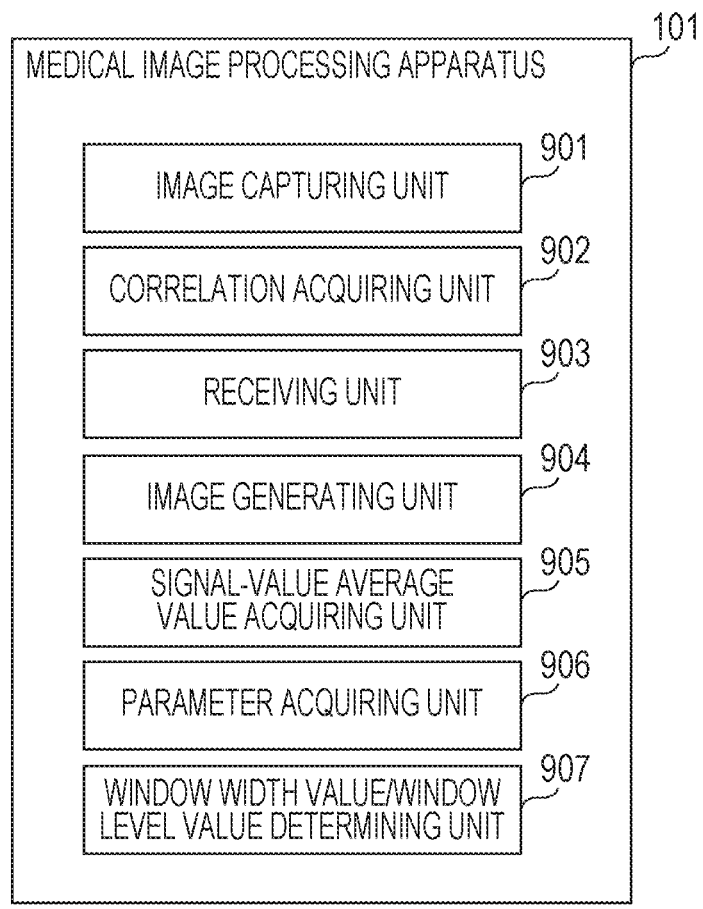
FIG. 9 is a configuration diagram illustrating a functional configuration of a medical image processing apparatus according to an implementation of a second exemplary embodiment.

FIG. 9 illustrates an exemplary functional configuration of the medical image processing apparatus 101 according to the second exemplary embodiment.

The medical image processing apparatus 101 includes an image acquiring unit 901, a correlation acquiring unit 902, a receiving unit 903, an image generating unit 904, a signal mean value acquiring unit 905, a parameter acquiring unit 906, and a window width value/window level value determining unit 907.

The image acquiring unit 901 is a function unit configured to acquire at least two MRI images of an identical part (identical cross section) of an object captured by an MRI apparatus in mutually different relaxation times (radiographing conditions). The correlation acquiring unit 902 is a function unit configured to acquire a correlation between a signal value and a relaxation time for each pixel based on the at least two MRI images acquired by the image acquiring unit 901. The receiving unit 903 is a function unit configured to receive a virtual relaxation time (virtual radiographing conditions) designated by a user. The image generating unit 904 is a function unit configured to generate a radiogram interpretation image C based on the correlation acquired by the correlation acquiring unit 902 and the virtual relaxation time received by the receiving unit 903. From the generated radiogram interpretation image C, a signal value of each pixel is acquired. The signal mean value acquiring unit 905 is a function unit configured to calculate and acquire a mean value of signal values (or signal mean value) of an MRI image and a mean value of signal values (or signal mean value) of the radiogram interpretation image generated by the image generating unit 904. The parameter acquiring unit 906 is a function unit configured to acquire a window width value and a window level value for displaying an MRI image. The window width value/window level value determining unit 907 is a function unit configured to determine a window level width and a window level value for displaying the radiogram interpretation image generated by the image generating unit 904 based on the mean value of signal values of the MRI image acquired by the signal mean value acquiring unit 905, the mean value of signal values of the radiogram interpretation image generated by the image generating unit 904, and the window width value and window level value acquired by the parameter acquiring unit 906.

The functional configuration of the medical image processing apparatus 101 illustrated in FIG. 9 has been described above.

Figure 10:
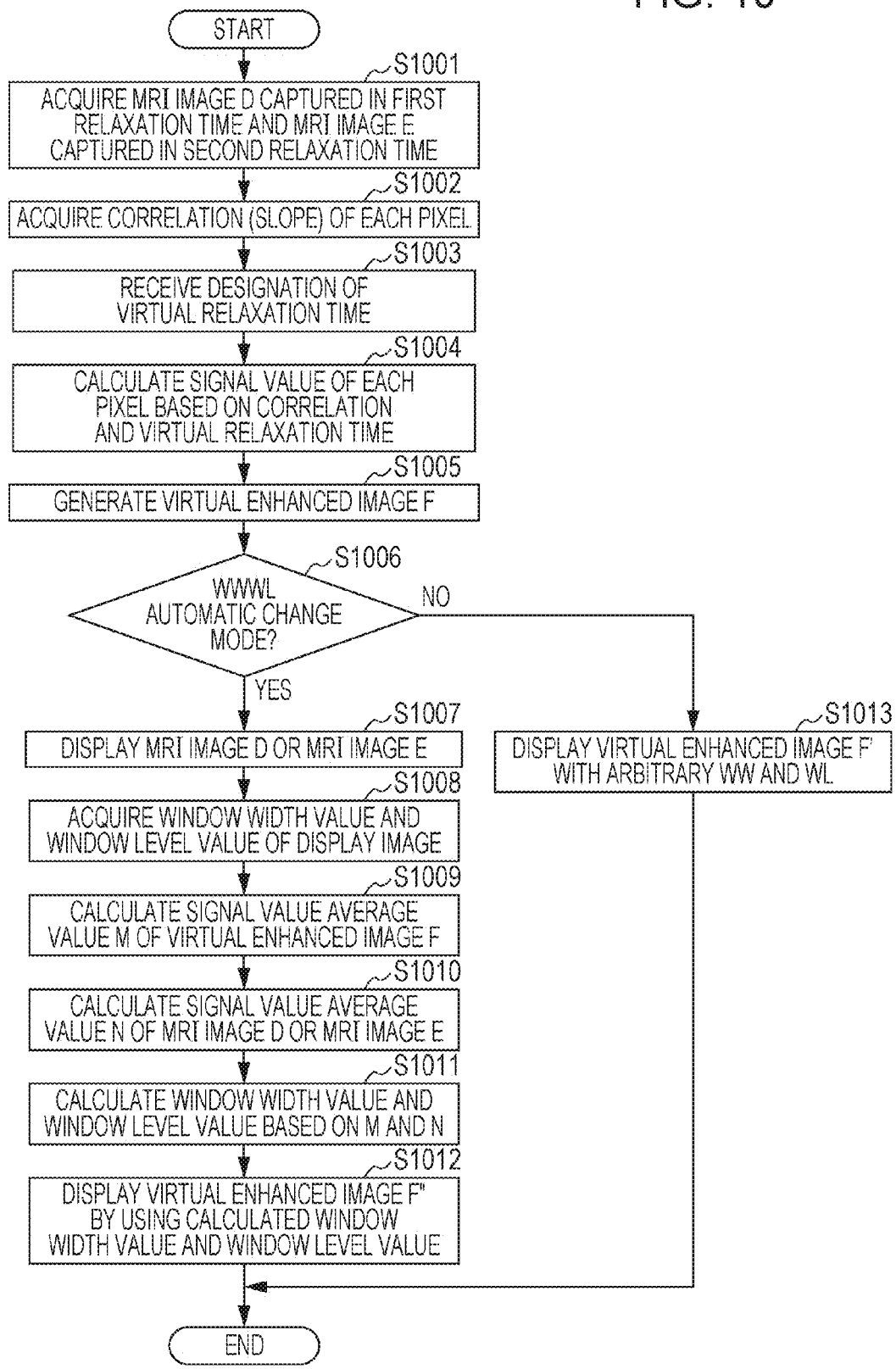
FIG. 10 is a flowchart illustrating a flow of processing for generating an image for radiogram interpretation according to an implementation of the second exemplary embodiment.

Next, with reference to the flowchart in FIG. 10, detail processing according to the second exemplary embodiment will be described.

First, a user may perform processing for reading desired volume data. More specifically, the CPU 201 in the medical image processing apparatus 101 acquires from an external storage device (not illustrated) MRI image data acquired by a medical image diagnosis apparatus such as an MRI apparatus and designated by a user. The MRI image data to be acquired here are at least two volume data sets acquired by capturing one object in mutually different relaxation times at substantially same times, and each of the volume data sets (three-dimensional medical image data sets) includes a plurality of slice images (two-dimensional images). The thus acquired volume data sets are stored in an external storage device (not illustrated) here but may be stored in a storage unit (external memory 211) of the medical image processing apparatus 101.

In step S1001, the CPU 201 in the medical image processing apparatus 101 acquires two MRI images (T2 enhanced images) captured in mutually different relaxation times corresponding to an identical position (identical cross section) designated by a user from the volume data (image acquiring unit). In the following description of the second exemplary embodiment, the two images are an MRI image D captured in a first relaxation time (12.72 msec) illustrated in FIG. 14A and an MRI image F captured in a second relaxation time (38.16 msec) illustrated in FIG. 14B. The MRI images acquired here may be cross section images acquired by cutting out volume data at an arbitrary plane.

In step S1002, the CPU 201 in the medical image processing apparatus 101 acquires a correlation between a signal value and a relaxation time of a pixel at identical coordinates on the MRI image D and the MRI image F acquired in step S1001 (correlation acquiring unit.). FIG. 13 illustrates a correlation between signal value (natural logarithms) and relaxation time of a pixel at identical coordinates on the MRI image D and the MRI image E. FIG. 13 illustrates an example of a linear approximation of a signal is of a pixel at identical coordinates based on coordinates of two points. The correlation of signal values associated with a lateral relaxation shows that pixels having a less inclination contain more water molecules. Having described that, according to the second exemplary embodiment, changes in signal value associated with a lateral relaxation is used as a correlation, changes in signal value associated with a longitudinal relaxation may be used as a correlation. The correlation to be acquired in step S1002 may be calculated for all pixels within a MRI image but may be calculated only for pixels having a predetermined signal value or higher.

Figure 12:
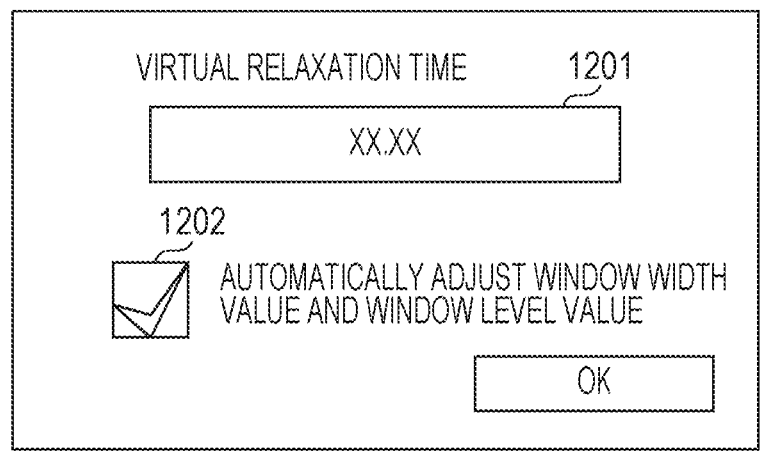
FIG. 12 illustrates a screen example illustrating an example of a screen for setting a virtual relaxation time according to the second exemplary embodiment.

In step S1003, the CPU 201 in the medical image processing apparatus 101 receives a virtual relaxation time designated by a user through a virtual-relaxation-time setting screen 1200 illustrated in FIG. 12 (receiving unit). The virtual-relaxation-time setting screen 1200 has a virtualrelaxation-time entry field 1201 and a check box area 1202 for setting automatic adjustment of a window width value and a window level value. The virtual-relaxation-time setting screen 1200 is given for illustration purpose, and an embodiment of the present invention is not limited thereto. Also for a virtual relaxation time, a time may not be entered, but a rate to a difference in relaxation time between the MRI image D and the MRI image E may be designated. From another point of view, in step S1003, the CPU 201 in the medical image processing apparatus 101 receives a virtual radiographing condition designated by a user. The virtual relaxation time is an example of the virtual radiographing condition.

In step S1004, the CPU 201 in the medical image processing apparatus 101 acquires a signal value of each pixel based on the correlation calculated in step S1002 and the virtual relaxation time received in step S1003. Referring to FIG. 13, a signal value for "XX.XX" designated by a user is calculated for each pixel, and signal values of all pixels are calculated in a case where the correlations are acquired for pixels having a predetermined signal value or higher in step S1002, signal values of the pixels may only be acquired. Thus, the load of performing image processing can be reduced.

In step S1005, the CPU 201 in the medical image processing apparatus 101 generates a virtual enhanced image F from signal values of pixels corresponding to the virtual relaxation time calculated in step 31004 (image generating unit). The virtual enhanced image F is an example of a diagnosis image.

In step S1006, the CPU 201 in the medical image processing apparatus 101 determines whether an automatic changing mode is set by a user for a window width value and a window level value or not. More specifically, if the check box area 1202 is selected in step S1003, it is determined that the automatic changing mode is set. If it is determined that the automatic changing mode is set, the processing moves to step S1007. If not, the processing moves to step S1013. However, the determination in step S1006 is not required in the second exemplary embodiment, and the processing in steps S1007 to 1012 may be performed or the processing in step S1013 may be performed without performing the determination.

In step S1013, the CPU 201 in the medical image processing apparatus 101 displays the virtual enhanced image F according to an arbitrary window width value and an arbitrary window level value. FIG. 15A illustrates the virtual enhanced image F displayed here. FIG. 15A illustrates a region 801 having water molecules displayed in an enhanced manner and more clearly than the region 801 in the two T2 enhanced images in FIGS. 14A and 14B. When a desired tissue is not enhanced in the image in FIG. 15A displayed according to an arbitrary window width value and an arbitrary window level value, a user such as a radiologist adjusts the window width value and the window level value and performs radiogram interpretation based on the virtual enhanced image F being an image which can be easily compared with a surrounding tissue with a modulated gray scale contrast as illustrated in FIG. 15B.

Figure 14A:
FIG. 14A exemplarily illustrates an MRI image D at relaxation time: 12.72 [ms], and FIG. 14B exemplarily illustrates an MRI image at a relaxation time: 38.16 [ms].
Figure 14B:
Figure 15A:
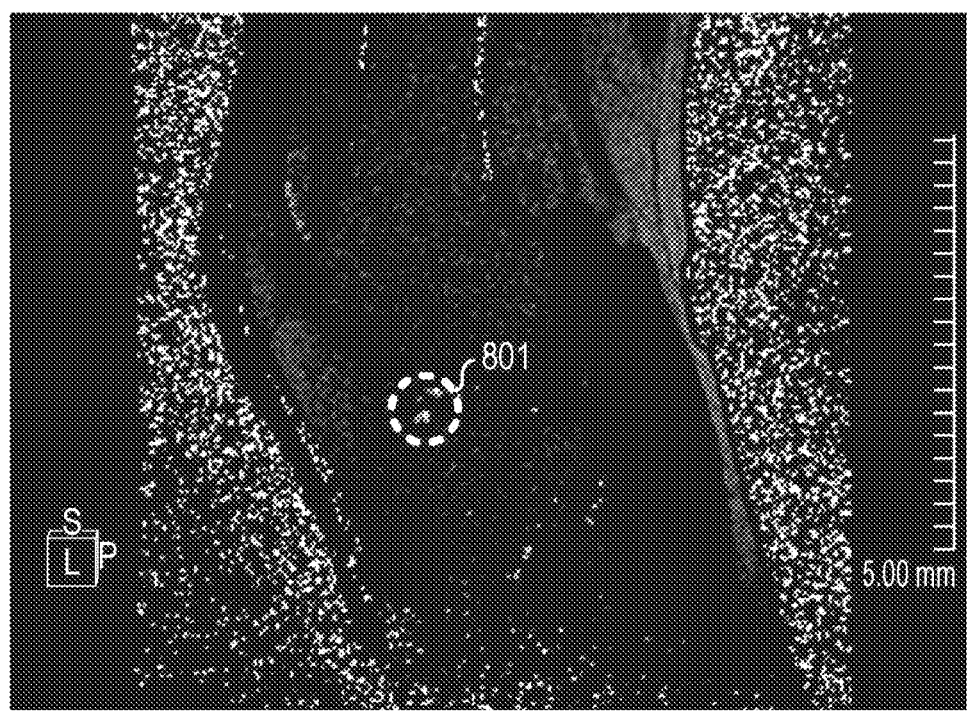
FIG. 15A exemplarily illustrates a virtual enhanced image F displayed with an arbitrary window level width value and window level value.
Figure 15B:
FIG. 15B exemplarily illustrates the virtual enhanced image F displayed with a window level width value and window level value determined based on a window level width value and a window level value set by a user.

Under a condition with a proper window width value WW and window level value WL of the virtual enhanced image F, a tissue which has not been identified easily from the original image illustrated in FIGS. 14A and 14B can be displayed in an enhanced manner. In other words, a radiogram interpretation image showing a desired tissue in an enhanced manner can be provided without capturing an object again by an MRI apparatus.

Figure 11:
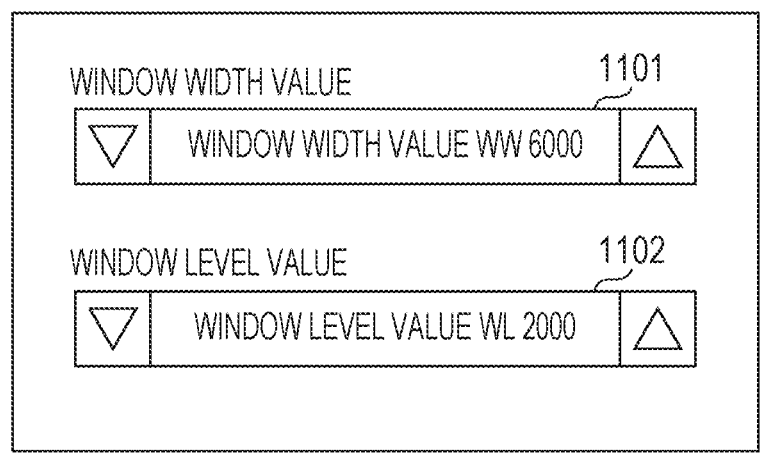
FIG. 11 illustrates a screen example illustrating a screen for setting a window width value and a window level value according to the second exemplary embodiment.

In step S1007, the CPU 201 in the medical image processing apparatus 101 displays the MRI image D or the MRI image E according to an arbitrary window width value and window level value designated by a user on the display device 210. For example, settings are received from a user in a window-width-value setting field 1101 and a window-level-value setting field 1102 on a window width value/window level value setting screen 1100 illustrated in FIG. 11. A user may set the window width value and window level value so that an MRI image having a contrast by which the user can perform radiogram interpretation more easily can be displayed. The image to be used by a user for setting the window width value WW and window level value WL may only be required to be an MRI image corresponding to an identical cross section of one patient and enhancing an identical type of relaxation and may be other images excluding the MRI image D and the MRI image E.

In step S1008, the CPU 201 in the medical image processing apparatus 101 acquires the window width value and the window level value set by the user in step S1007 (parameter acquiring unit).

In step S1009, the CPU 201 in the medical image processing apparatus 101 calculates and acquires a signal mean value M being a mean value of signal values of the virtual enhanced image F generated in step S1005 (signal mean value acquiring unit).

In step S1010, the CPU 201 in the medical image processing apparatus 101 acquires a signal mean value N of the MRI image D or MRI image F displayed in step S1007 (signal mean value acquiring unit).

The pixels to be used for calculating the signal mean value N and signal mean value N may not be required to be all pixels of an image. It may only be required that the position coordinates of a pixel used for acquiring the signal mean value M in step S1009 are matched with those of a pixel used for acquiring the signal mean value N in step S1010. Therefore, for example, the signal mean value N may correspond to a pixel having a predetermined signal value or higher of the MRI image displayed in step S1007, and the signal mean value M may correspond to a pixel having a predetermined signal value or higher of the virtual enhanced image F generated in step S1005.

In step S1011, the CPU 201 in the medical image processing apparatus 101 acquires the window width value and window level value for the virtual enhanced image based on the signal mean value M calculated in step S1009 and the signal mean value N calculated in step S1010 (determining unit). More specifically, the signal mean value M/signal mean value N is acquired by dividing the signal mean value M acquired by the calculation in step S1009 by the signal mean value N acquired by the calculation in step S1010. The signal mean value M/signal mean value N is then multiplied by the window width value and window level value acquired in step S1008 to acquire the window width value and window level value of the virtual enhanced image F.

In step S1012, the CPU 201 in the medical image processing apparatus 101 displays the virtual enhanced image F generated in step S1005 in accordance with the window width value and window level value acquired in step S1012 (display unit). An example of the virtual enhanced image F to be displayed is the virtual enhanced image F" in FIG. 15B. As illustrated in FIG. 15B, a part enhancing water molecules like the region 802 is displayed more clearly than the two T2 enhanced images in FIGS. 7A and 7B. Furthermore, the image can be a radiogram interpretation image having a contrast allowing comparison between 802 and other tissues, by which a user can perform radiogram interpretation more easily. The automatic adjustment of the window width value and window level value allows display of the virtual enhanced image F (radiogram interpretation image) based on the window width value and window level value set by a user for easy visual recognition without requiring the user to take time and effort for adjustment of the window width value and window level value. Such a virtual enhanced image displays, in an enhanced manner, a tissue which has not been identified easily from the original image illustrated in FIGS. 14A and 14B so that a radiogram interpretation image enhancing a desired tissue can be acquired without capturing the object again by an MRI apparatus.

Having described that, according to the second exemplary embodiment, a relaxation time is defined as an example of radiographing conditions, the radiographing condition may be an inversion time in inversion recovery.

Having described that, according to the second exemplary embodiment, pixels of two-dimensional images are used to generate a virtual enhanced image (virtual image in a virtual relaxation time) of the two-dimensional images, an enhanced image can be generated from voxels. In other words, a correlation may be acquired between voxels at identical coordinates in three-dimensional medical images, and a signal value of the voxel in a virtual relaxation time is acquired in accordance with the correlation to generate a virtual enhanced image.

Having described that, according to the second exemplary embodiment, two of the MRI image D captured in a relaxation time (12.72 msec) and the MRI image E captured in a relaxation time (38.16 msec) substantially at a same time are used to acquire a correlation, MRI images captured in other relaxation times may be used to acquire a correlation. Three or more MRI images captured in mutually different relaxation times may be used to acquire a correlation. The correlation may be not only a function acquired by linear approximation but also a function acquired by exponential approximation, logarithmic approximation, polynomial approximation, or moving averaging.

Having described that, according to the second exemplary embodiment, both of the window width value (WW) and the window level value (WL) are adjusted, only one of them may be adjusted.

As described above, in the medical image processing apparatus according to the second exemplary embodiment, a mechanism may be provided which can provide a desired radiogram interpretation image without capturing an object again by an MRI apparatus.

Other Embodiments

The present invention can be embodied as a system, an apparatus, a method, a program or a storage medium, for example. More specifically, it is applicable to a system including a plurality of apparatuses or an apparatus including one device. An embodiment of the present invention can be also achieved by supplying a software program which implements a function of the aforementioned embodiment directly or remotely to the system or apparatus. An embodiment which is achieved by reading out and executing the supplied program code by an information processing apparatus in the system or apparatus is also included in the present invention.

Therefore, the present invention can also be implemented by program code itself to be installed in the information processing apparatus for implementing function processing of the present invention in the information processing apparatus. In other words, the present invention may also include a computer program itself for implementing the function processing of the present invention.

In this case, the present invention may be embodied by object code, a program executed by an interpreter, script data supplied to an OS or the like if it has a function of the program.

The program may be supplied in a recording medium such as a flexible disk, a hard disk, an optical disk, a magneto-optical disk, an MO, a CD-ROM, a CD-R, and a CD-RW. The recording medium may further be a magnetic tape, a nonvolatile memory card, a ROM, a DVD (DVD-ROM, DVD-R) or the like.

In addition, the program may be supplied from a web site accessible over the Internet through a browser of a client computer. The computer program of the present invention itself or a compressed file of the computer program including an automatic install function may be downloaded to a recording medium such as a hard disk.

The program code of the present invention may be divided into a plurality of files so that the files can be downloaded, from different web sites. In other words, the present invention further includes a WWW server from which a plurality of users can download the program file for implementing the function processing of the present invention in an information processing apparatus.

The program of the present invention may be encrypted, be stored in a storage medium such as a CD-ROM and be distributed to a user. A user who satisfies a predetermined condition is allowed to download key information for solving the encryption from a web site over the Internet. By using the downloaded key information, the encrypted program may be executed to be installed in an information processing apparatus for implementation.

The functions of the aforementioned embodiments may be realized by an information processing apparatus by reading out and executing the program. In addition, an OS running on an information processing apparatus may implement a part or all of actual processes based on instructions from the program so that the processes can realize the functions of the aforementioned embodiments.

Furthermore, the program read out from a recording medium may be written in a memory provided in a function expanding board inserted to an information processing apparatus or function expanding unit connected to an information processing apparatus. After that, a CPU provided in the function expanding board or function expanding unit may execute a part or all of actual processes based on instructions from the program so that the processes can realize the functions of the aforementioned embodiments.

It should be understood that the aforementioned embodiments are given only for purpose of illustration of specific examples for embodying the present invention, and it should not be interpreted that the technical scope of the present invention is limited thereby. In other words, the present invention may be embodied in various forms without departing from the technical idea or main features of the present invention.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (PD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-174592, filed Sep. 4, 2015, and Japanese Patent Application No. 2015-175036, filed Sep. 4, 2015, which are hereby incorporated by reference herein in their entirety.

What is claimed is:

1. A medical image processing apparatus comprising:
an image acquiring unit configured to acquire a plurality of medical images obtained by imaging an identical region of an object under different radiographing conditions;
a relation acquiring unit configured to acquire a correlation between a signal value and a radiographing condition at a pixel at a same position in the plurality of medical images;
a condition acquiring unit configured to acquire a virtual radiographing condition that is different from the radiographing conditions of the plurality of medical images;
a generating unit configured to generate a diagnosis image by acquiring a signal value of each pixel based on the correlation and the virtual radiographing condition;
a display condition acquiring unit configured to acquire a window width value and a window level value for displaying one medical image of an identical cross section of the object; and
a display control unit configured to cause a display unit to display the diagnosis image based on the window width value and window level value acquired by the display condition acquiring unit.

2. The medical image processing apparatus according to claim 1, further comprising a mean value calculating unit configured to acquire a mean value of signal values of the one medical image corresponding to at least one of the window width value and window level value acquired by the display condition acquiring unit and a mean value of signal values corresponding to the diagnosis image generated by the generating unit,
wherein the display control unit is configured to display the diagnosis image on the display unit based on a window width value and a window level value obtained by multiplying the window width value and window level value acquired by the display condition acquiring unit by a reciprocal of the mean value of the signal values of the one medical image calculated by the mean value calculating unit and the mean value of the signal values corresponding to the diagnosis image.

3. The medical image processing apparatus according to claim 1, wherein the relation acquiring unit is configured to acquire the correlation for all pixels of the medical image acquired by the image acquiring unit.

4. The medical image processing apparatus according to claim 1, wherein the relation acquiring unit is configured to acquire the correlation by using information regarding partial pixels of the medical image acquired by the image acquiring unit.

5. The medical image processing apparatus according to claim 1,
wherein the image acquiring unit is configured to acquire a plurality of CT images at an identical position of the object under different radiographing conditions; and
the radiographing conditions are X-ray tube voltages.

6. The medical image processing apparatus according to claim 5, wherein the plurality of CT images are CT images captured after a contrast agent is administered to the object.

7. The medical image processing apparatus according to claim 5, wherein the relation acquiring unit is configured to acquire a correlation between a difference in CT value and the X-ray tube voltage.

8. The medical image processing apparatus according to claim 1,
wherein the image acquiring unit is configured to acquire a plurality of MRI images of an identical position of the object captured under different radiographing conditions; and
the radiographing conditions are relaxation times.

9. The medical image processing apparatus according to claim 8, wherein the relation acquiring unit is configured to acquire a correlation between natural logarithms of signal values and the relaxation times.

10. The medical image processing apparatus according to claim 1,
wherein the image acquiring unit is configured to acquire a plurality of MRI images of an identical position of the object captured under different radiographing conditions; and
the radiographing conditions are inversion times.

11. A medical image processing method comprising:
acquiring a plurality of medical images obtained by imaging an identical region of an object under different radiographing conditions;
acquiring a correlation between a signal value and a radiographing condition at a pixel at a same position in the plurality of medical images;
acquiring a virtual radiographing condition that is different from the radiographing conditions of the plurality of medical images;
generating a diagnosis image by acquiring a signal value of each pixel based on the correlation and the virtual radiographing condition;
acquiring a window width value and a window level value for displaying one medical image of an identical cross section of the object; and
causing a display unit to display the diagnosis image based on the window width value and window level value.

12. A medical image processing system comprising:
an image acquiring unit configured to acquire a plurality of medical images obtained by imaging an identical region of an object under different radiographing conditions;
a relation acquiring unit configured to acquire a correlation between a signal value and a radiographing condition at a pixel at a same position in the plurality of medical images;
a condition acquiring unit configured to acquire a virtual radiographing condition that is different from the radiographing conditions of the plurality of medical images;
a generating unit configured to generate a diagnosis image by acquiring a signal value of each pixel based on the correlation and the virtual radiographing condition;
a display condition acquiring unit configured to acquire a window width value and a window level value for displaying one medical image of an identical cross section of the object; and
a display control unit configured to cause a display unit to display the diagnosis image based on the window width value and window level value acquired by the display condition acquiring unit.

13. A medical image processing apparatus comprising:
a memory storing instructions; and
at least one processor that, upon execution of the instructions is configured to
  acquire a plurality of medical images obtained by imaging an identical region of an object under different radiographing conditions;
  acquire a correlation between a signal value and a radiographing condition at a pixel at a same position in the plurality of medical images;
  acquire a virtual radiographing condition that is different from the radiographing conditions of the plurality of medical images;
  generate a diagnosis image by acquiring a signal value of each pixel based on the correlation and the virtual radiographing condition;
  acquire a window width value and a window level value for displaying one medical image of an identical cross section of the object; and
  cause a display unit to display the diagnosis image based on the window width value and window level value acquired by the display condition acquiring unit.

14. A medical image processing apparatus comprising:
an image acquiring unit configured to acquire a plurality of medical images obtained by imaging an identical region of an object under different radiographing conditions;
a relation acquiring unit configured to acquire a correlation between a signal value and a radiographing condition at a pixel at a same position in the plurality of medical images;
a condition acquiring unit configured to acquire a virtual radiographing condition that is different from the radiographing conditions of the plurality of medical images;
a generating unit configured to generate a diagnosis image by acquiring a signal value of each pixel based on the correlation and the virtual radiographing condition;
a display condition acquiring unit configured to acquire a window width value and a window level value for displaying one medical image of an identical cross section of the object; and
a mean value calculating unit configured to acquire a mean value of signal values of the one medical image corresponding to at least one of the window width value and window level value acquired by the display condition acquiring unit and a mean value of signal values corresponding to the diagnosis image generated by the generating unit
a display control unit to display the diagnosis image on the display unit based on a window width value and a window level value obtained by multiplying the window width value and window level value acquired by the display condition acquiring unit by a reciprocal of the mean value of the signal values of the one medical image calculated by the mean value calculating unit and the mean value of the signal values corresponding to the diagnosis image,
wherein the image acquiring unit is configured to acquire a plurality of CT images at an identical position of the object under different radiographing conditions; and
the radiographing conditions are X-ray tube voltages.

* * * * *